(12) United States Patent
Rota et al.

(10) Patent No.: US 9,801,696 B2
(45) Date of Patent: Oct. 31, 2017

(54) INSTRUMENT FOR DRILLING DENTAL ROOT CANALS

(71) Applicant: MAILLEFER INSTRUMENTS HOLDING SARL, Ballaigues (CH)

(72) Inventors: Gilbert Rota, Vaux et Chantegrue (FR); Paul-Henri Vallotton, Pampigny (CH)

(73) Assignee: MAILLEFER INSTRUMENTS HOLDING SÁRL, Ballaigues (CH)

(*) Notice: Subject to any disclaimer, the term of this patent is extended or adjusted under 35 U.S.C. 154(b) by 0 days.

(21) Appl. No.: 14/651,677

(22) PCT Filed: Jun. 7, 2013

(86) PCT No.: PCT/IB2013/001191
§ 371 (c)(1),
(2) Date: Jun. 12, 2015

(87) PCT Pub. No.: WO2014/118591
PCT Pub. Date: Aug. 7, 2014

(65) Prior Publication Data
US 2015/0320517 A1   Nov. 12, 2015

(30) Foreign Application Priority Data
Jan. 30, 2013   (WO) .................. PCT/IB2013/000108

(51) Int. Cl.
A61C 5/00 (2017.01)
A61C 5/02 (2006.01)
A61C 5/42 (2017.01)

(52) U.S. Cl.
CPC ............... *A61C 5/023* (2013.01); *A61C 5/42* (2017.02)

(58) Field of Classification Search
CPC .................................. A61C 5/023; A61C 5/42
See application file for complete search history.

(56) References Cited

U.S. PATENT DOCUMENTS

| 4,842,451 A | 6/1989 | Dugger |
| 5,503,554 A | 4/1996 | Schoeffel |
| (Continued) | | |

FOREIGN PATENT DOCUMENTS

| DE | 102006007316 A1 | 8/2007 |
| EP | 0120542 A1 | 10/1984 |
| (Continued) | | |

OTHER PUBLICATIONS

International Search Report, dated Sep. 13, 2013, from corresponding PCT application.
(Continued)

Primary Examiner — Eric D. Bertram
(74) Attorney, Agent, or Firm — Young & Thompson (57) ABSTRACT

An instrument for drilling dental root canals includes a tapered rod having over at least a part of its length—the active part—a polygonal cross-section forming at least two cutting edges, the active part terminating by a point and being defined by an envelope of cylindrical or conical shape, whose longitudinal axis coincides with the instrument's axis of rotation. The active part has a first portion extending from the point and a second portion extending following the first portion towards the rear of the active part. At least one cross-section of the first portion has a center of mass located on the axis of rotation and the cutting edges are located on the envelope. Any cross-section of the second portion has a center of mass offset with respect to the axis of rotation and at least one cutting edge defined by the cross-section is located set back.

10 Claims, 4 Drawing Sheets

(56) References Cited

U.S. PATENT DOCUMENTS

| | | |
|---|---|---|
| 5,775,904 A | 7/1998 | Riitano |
| 5,836,764 A | 11/1998 | Buchanan |
| 5,921,775 A | 7/1999 | Buchanan |
| 5,938,440 A | 8/1999 | McSpadden |
| 6,106,296 A | 8/2000 | Johnson |
| 6,702,579 B1 | 3/2004 | Hoppe et al. |
| 7,955,078 B2 | 6/2011 | Scianamblo |
| 2004/0023186 A1 | 2/2004 | McSpadden |
| 2004/0219485 A1 | 11/2004 | Scianamblo |
| 2005/0100859 A1 | 5/2005 | Graybill et al. |
| 2005/0282109 A1 | 12/2005 | Hagemann |
| 2006/0111724 A1 | 5/2006 | Yeung |
| 2006/0228668 A1* | 10/2006 | McSpadden ........... A61O 5/023 433/102 |
| 2006/0228669 A1 | 10/2006 | Scianamblo |
| 2006/0265858 A1* | 11/2006 | McSpadden ........... A61C 5/023 29/558 |
| 2007/0015107 A1 | 1/2007 | Mannschedel et al. |
| 2012/0034048 A1 | 2/2012 | Krieg et al. |

FOREIGN PATENT DOCUMENTS

| | | |
|---|---|---|
| EP | 0987076 A2 | 3/2000 |
| EP | 1184004 A2 | 3/2002 |
| EP | 1213074 A2 | 6/2002 |
| EP | 1340573 A1 | 9/2003 |
| EP | 1361831 A1 | 11/2003 |
| FR | 2798277 A1 | 3/2001 |
| FR | 2854054 A1 | 10/2004 |
| FR | 2935260 A1 | 3/2010 |
| JP | 52-156494 A | 12/1977 |
| JP | 57-127608 A | 8/1982 |
| JP | 62-241606 A | 10/1987 |
| JP | H06-320323 A | 11/1994 |
| JP | 11-019812 A | 1/1999 |
| JP | 2002-144122 A | 5/2002 |
| JP | 2002-205213 A | 7/2002 |
| JP | 2009502349 | 1/2009 |
| JP | 2009-108382 A | 5/2009 |
| SU | 637207 A1 | 12/1978 |
| WO | 01/19279 A1 | 3/2001 |
| WO | 02/065938 A1 | 8/2002 |
| WO | 2004/098438 A1 | 11/2004 |
| WO | WO2009001681 A1 | 8/2010 |
| WO | 2012038437 | 3/2012 |
| WO | 2014/118587 A1 | 8/2014 |

OTHER PUBLICATIONS

Japanese Office Action dated Jan. 18, 2017; Application No. 2015-554257.
European Office Action issued in Application No. 06007527.2, dated Jun. 17, 2009.
European Office Action issued in Application No. 04750878.3, dated Jun. 5, 2007.
European Office Action issued in Application No. 04751290.0, dated Jun. 5, 2007.
International Search Report and Written Opinion issued in Application No. PCT/US2014/051916, dated Feb. 4, 2015.
International Search Report and Written Opinion issued in Application No. PCT/US2014/051909, dated Dec. 22, 2014.
European Office Action issued in Application No. 06007527.2, dated Jul. 6, 2004.
"ProTaper Next: A Shift Up in Performance," ProTaper Next Rotary Files, Jan. 2013, 1 pages.
European Search Report issued in Application No. 14838210.4, dated Mar. 8, 2014.
"Drilling Through Walls," Ultimate Handyman, YouTube, <URL: https://www.youtube.com/watch?v=fpFUxlcH2Lg>, Sep. 23, 2011, retrieved from the internet Aug. 24, 2017, 3 pages.

* cited by examiner

INSTRUMENT FOR DRILLING DENTAL ROOT CANALS

BACKGROUND OF THE INVENTION

Field of the Invention

The object of the present invention is an instrument for drilling dental root canals.

Description of the Related Art

The treatment of an infected dental root is carried out by extracting the pulp using special instruments, then by shaping the root canal using successive drilling procedures, traditionally carried out with instruments of varying size and conicity. The final operation consists of filling the root canal.

The shaping of the root canal consists initially of enlarging the canal in its crown and medial parts to permit, as a second step, easier treatment of the apical part of the canal by mechanical cleaning the infected tissues.

An instrument designed for drilling dental root canals generally has a tapered rod fitted into a handle to permit it to be driven manually or mechanically and comprising, on at least part of its length, helicoidal flutes with a constant or non-constant pitch, and having at least one cutting edge.

Used in continuous rotation, this type of instrument may have a tendency to screw itself into the canal. Apart from the screwing action, another problem occurring in the production of instruments for drilling root canals is that of the strength and flexibility of the instruments. Indeed, when the instrument is too flexible it may bend or break before the practitioner has been able to complete the operation and when the instrument is too rigid, it follows the curvature of the dental root canal only with difficulty.

Numerous instruments have been developed in response to these problems. Document EP 1 361 831 describes an instrument for drilling dental canals comprising a base, a cutting section and a guiding section, the cutting section being defined by an envelope of a cylindrical or conical shape, the longitudinal axis of which coincides with the axis of rotation of the instrument. The cutting section has clearance zones disposed set-back with respect to the envelope, alternating with drilling zones disposed on said envelope.

This alternating arrangement of zones on the envelope and set back from the envelope makes it possible to reduce the risk of screwing the instrument into the dental canal. Furthermore, the axis of the cutting section can be offset with respect to the axis of the envelope. This makes it possible to deepen the clearance zones and to make the evacuation of the debris during treatment more effective.

Document U.S. Pat. No. 7,955,078 describes an endodontic instrument for preparation of dental root canals comprising a body shaped to turn about an axis of rotation. The body has a centre of mass which is not located on the axis of rotation of the instrument, thus giving the impression that the instrument is undulating ("swaggering") when it is rotated. An instrument such as this has greater flexibility and thus makes it possible to follow the complex curves of a dental root canal most effectively.

However, in these two documents the axis of the active part is offset with respect to the axis of rotation of the instrument over the whole length of said active part and in particular the axis of the point of the instrument is offset. This can generate a beating motion of the point within the canal. It thus becomes difficult to ensure optimum dimensioning of the canal during treatment, in particular in its apical portion. Moreover, a point with its axis offset also has the disadvantage of pushing the debris back towards the apical portion rather than evacuating it towards the top of the canal.

The aim of the present invention is to produce an instrument for drilling dental root canals which obviates the stated disadvantages. In particular, one aim of the present invention is thus to produce an instrument which is flexible while being strong, reliable and effective and which makes it possible at the same time to respect the initial path of the root canal to be treated and to ensure optimum dimensioning of the canal in its apical portion after treatment.

BRIEF SUMMARY OF THE INVENTION

The object of the present invention is an instrument for drilling dental root canals.

BRIEF DESCRIPTION OF THE DRAWINGS

The drawings schematically illustrate by way of example a plurality of embodiments of the instrument in accordance with the invention.

DETAILED DESCRIPTION OF THE PREFERRED EMBODIMENTS

Figure 1:
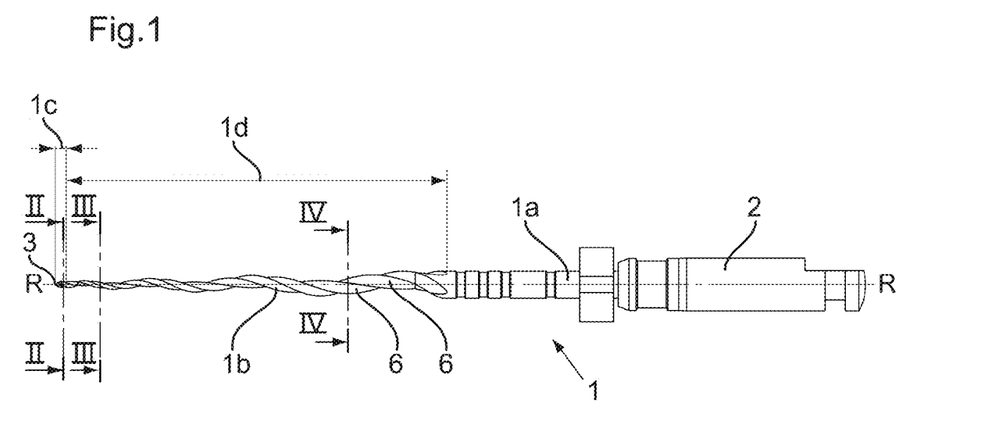
FIG. 1 illustrates a first embodiment of an instrument for drilling dental root canals in accordance with the invention.

In a first embodiment shown in FIG. 1 the instrument in accordance with the invention comprises a rod 1 fitted at one of its ends 1a in a handle 2 permitting either manual actuation of the instrument or preferably its engagement in a hand-held part providing mechanical driving of the said instrument. In particular, the instrument 1 is intended to be driven in rotation about its axis of rotation R.

The rod 1 has an active part 1b extending to the other end 3—the point 3—of the rod 1. Said active part 1b is preferably tapered and conical, narrowing to the point 3 of the rod 1. Alternatively, the active part 1b or the whole rod 1 could be cylindrical rather than conical.

The active part 1b has a polygonal cross-section (the sides of which are straight or curved) and comprises cutting edges. More particularly in this first embodiment, the active part 1b has, over its whole length, a square cross-section 4 forming four cutting edges 5a, 5b, 5c, 5d defining between them four helicoidal flutes 6, one flute being the face defined between two successive cutting edges of the active part 1b. The active part 1b is defined by an envelope 7 which is substantially tapered and has its longitudinal axis coinciding with the axis of rotation R of the instrument.

The particular feature of the instrument in accordance with the invention resides in the fact that the active part 1b has a first portion 1c extending from the point 3 towards the rear of the active part 1b and of which the centre of mass is located on the axis of rotation R of the instrument and a second portion 1d extending from the end of the first portion 1c to the rear of the active part 1b and of which at least one cross-section has a centre of mass which is not located on the axis of rotation R of the instrument but is offset with respect to said axis R. In the first embodiment shown in FIGS. 1 to 4, any cross-section of the second portion 1d of the active part 1b of the instrument 1 has a centre of mass which is not located on the axis of rotation R but is offset with respect to said axis.

Figure 2:
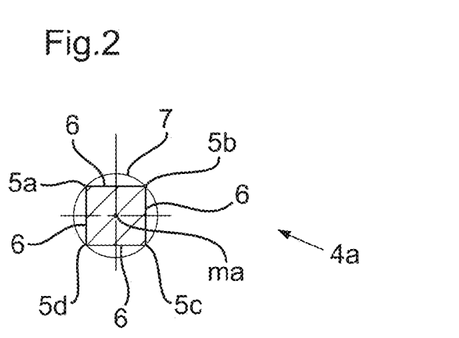
FIG. 2 is a cross-sectional view at the line II-II of the instrument shown in FIG. 1.

More precisely, and as shown in FIG. 2, in accordance with the invention any cross-section 4a of the first portion 1c has its centre of mass ma on the axis of rotation R of the instrument. Moreover, in this first embodiment the four edges 5a, 5b, 5c, 5d of such a cross-section 4a are located on the envelope 7. Thus the first portion 1c and in particular the point 3 are centred with respect to the axis of rotation R of the instrument or in other words the longitudinal axis of the first portion 1c coincides with said axis of rotation R.

Figure 3:
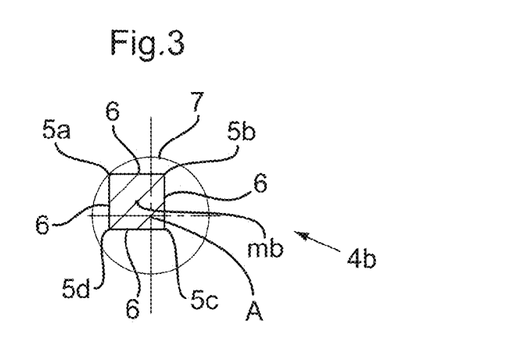
FIG. 3 is a cross-sectional view at the line III-III of the instrument shown in FIG. 1.
Figure 4:
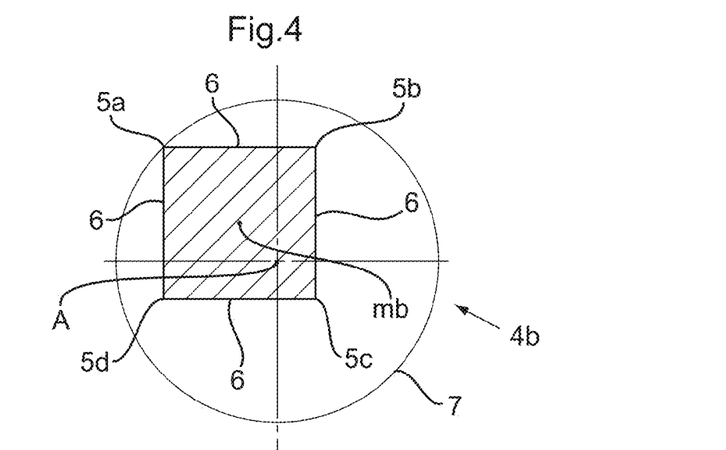
FIG. 4 is a cross-sectional view at the line IV-IV of the instrument shown in FIG. 1.

As shown in FIGS. 3 and 4, in the first embodiment, any cross-section 4b of the second portion 1d of the active part 1b has its centre of mass mb offset with respect to the axis of rotation R of the instrument and preferably a single cutting edge 5a of such a cross-section 4b is located on the envelope 7, the other cutting edges 5b, 5c and 5d being disposed inside said envelope 7. Thus in the first embodiment the whole of the second portion 1d of the active part 1b is off-centre with respect to the axis of rotation R of the instrument.

Thus an effective instrument is obtained because its point 3 is centred, does not generate any beating within the canal and has four active cutting edges.

Such an instrument in accordance with the invention can be obtained from a rod with a circular cross-section, preferably made from a nickel-titanium alloy, by providing therein helicoidal flutes by machining (milling), these flutes defining cutting edges such that the cross-section of the rod 1 is polygonal over the whole length of its active part 1b. In order to achieve the particular geometry of the active part 1b in accordance with the invention, the flutes 6 of the second portion 1d of the active part 1b are overcut with respect to the flutes 6 of the first portion 1c in order to obtain at least one cross-section 4b of said second portion 1d of which at least one cutting edge is set back within the envelope 7 and of which the centre of mass mb is offset with respect to the axis of rotation R. Thus on the second portion 1d of the active part 1b material is removed from the instrument in accordance with the invention, which makes it more flexible on this second portion than a traditional instrument which would have, over its whole active part, a cross-section with its centre of mass centred on the axis of rotation and all its edges inscribed on the envelope. By virtue of the present invention, an instrument is obtained which is effective at its point 3 while being flexible.

Preferably, in the first embodiment, the second portion 1d has a progressive offset with respect to the axis of rotation R in the direction of the rear of the instrument: i.e. a cross-section of the second portion 1d close to the point has its centre of mass less offset proportionally to the surface of the cross-section with respect to said axis of rotation R than a cross-section of the second portion 1d closer to the rear of the instrument. In terms of machining the instrument, this produces flutes 6 which are overcut proportionally more and more along the second portion 1d of the active part 1b with respect to the flutes of the first portion 1c. Thus in this first embodiment the flexibility of the instrument is adjustable and in particular increases progressively towards the rear of the active part 1b.

Preferably, the first portion 1c of the active part extends over a length of 3 millimeters starting from the point 3 of the active part 1b. In a still more preferred manner, said first portion 1c has a length of 1 millimeter.

Figure 5:
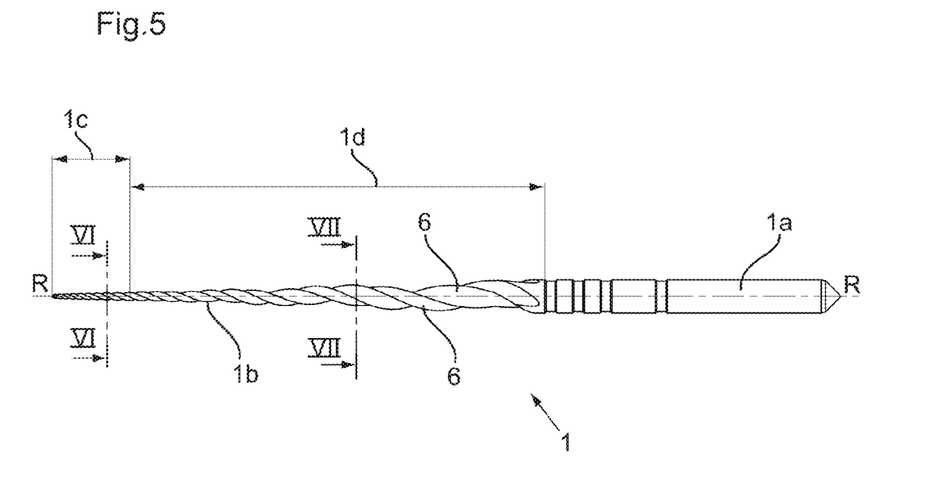
FIG. 5 illustrates a second embodiment of an instrument for drilling dental root canals in accordance with the invention.
Figure 6:
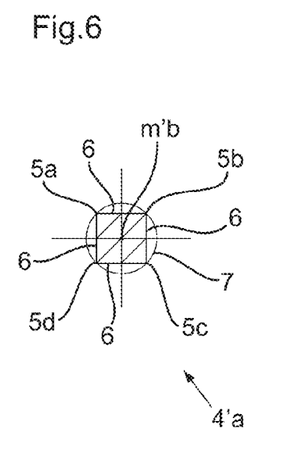
FIG. 6 is a cross-sectional view at the line VI-VI of the instrument shown in FIG. 5.
Figure 7:
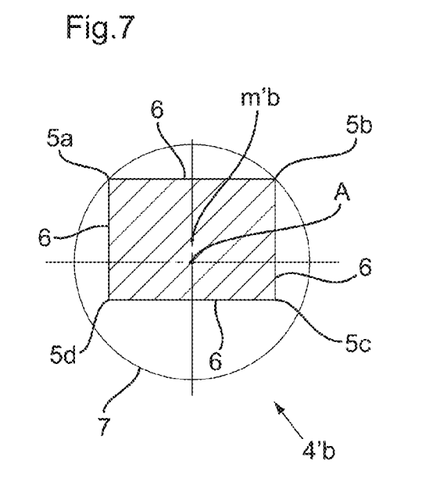
FIG. 7 is a cross-sectional view at the line VII-VII of the instrument shown in FIG. 5.

FIGS. 5 to 7 show a second embodiment of an instrument in accordance with the invention in which the active part 1b has, over its whole length, a rectangular cross-section 4' forming four cutting edges 5a, 5b, 5c, 5d defining four helicoidal flutes 6, one flute being the face defined between two successive cutting edges of the active part 1b. As in the first embodiment, the active part 1b is defined by an envelope 7 which is substantially tapered and has the axis of rotation R of the instrument as its longitudinal axis.

The active part 1b also has a first portion 1c extending from the point 3 towards the rear of the active part 1b and having its centre of mass located on the axis of rotation R of the instrument and a second portion 1d extending from the end of the first portion 1c to the rear of the active part 1b and of which at least one cross-section has a centre of mass offset with respect to the axis of rotation R of the instrument. Preferably, and as in the first embodiment, any cross-section of the second portion 1d of the instrument in accordance with the second embodiment has a centre of mass offset with respect to the axis of rotation R.

In this second embodiment, and as shown in FIG. 6, any cross-section 4'a of the first portion 1c is square and has its centre of mass m'a on the axis of rotation R of the instrument. Furthermore, the four edges 5a, 5b, 5c, 5d of such a cross-section 4'a are located on the envelope 7 of the instrument. As shown in FIG. 7, any cross-section 4'b of the second portion 1d of the active part 1b has its centre of mass m'b offset with respect to the axis of rotation R of the instrument. In contrast to the first embodiment, for each cross-section 4'b of the second portion 1d of the active part 1c of the instrument in accordance with the second embodiment, two cutting edges 5a and 5b are on the envelope 7, the two other cutting edges 5c and 5d being disposed inside said envelope 7.

The other considerations relating to the first embodiment remain valid for this second embodiment.

As shown in FIGS. 6 and 7, the cross-sections 4'a and 4'b of the first and second portions 1c, 1d are not necessarily symmetrical, the cross-section 4'a preferably being square, while the cross-section 4'b may be rectangular.

FIGS. 8 to 14 show a third embodiment of an instrument in accordance with the invention, in which the active part 1b of the instrument has, over its whole length, a polygonal cross-section 40 of a parallelogram shape, forming four cutting edges 51, 52, 53, 54 defining four helicoidal flutes 6, one flute being the face defined between two successive cutting edges of the active part 1b. As in the previous embodiments, the active part 1b is defined by an envelope 7 which is substantially tapered and has the axis of rotation R of the instrument as its longitudinal axis.

Figure 9:
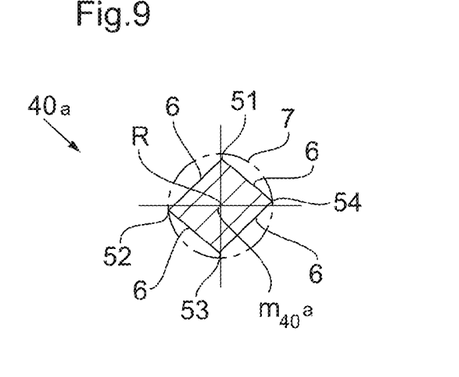
FIG. 9 is a cross-sectional view at the line A-A of the instrument shown in FIG. 8.

In accordance with the invention, the active part 1b has a first portion 1c extending from the point 3 towards the rear of the active part 1b and having its centre of mass located on the axis of rotation R of the instrument. In this third embodiment, and as shown in FIG. 9, any cross-section 40a of the first portion 1c is in the form of a parallelogram and has its centre of mass $m_{40}a$ on the axis of rotation R of the instrument. Moreover, in this embodiment, two diagonally opposed cutting edges 52, 54 of such a cross-section 40a are located on the envelope 7 of the instrument, while the other pair of diagonally opposed cutting edges 51, 53 is located set back within the envelope 7.

In accordance with the invention, the active part 1b also has a second portion 1d extending from the end of the first portion 1c to the rear of the active part 1b, of which at least one cross-section has a centre of mass which is not located on the axis of rotation R of the instrument but which is offset with respect to said axis R. In the third embodiment of the invention, and as shown in FIGS. 8 and 10 to 14, the second portion 1d has an alternating arrangement of first zones—off-centre zones 11—in which any cross-section 401b has a centre of mass $m_{401}b$ offset with respect to the axis of rotation R of the instrument and second zones—centred zones 12—in which any cross-section 402b has a centre of mass $m_{402}b$ located on the axis of rotation R of the instrument. The zone of the second portion 1d directly adjacent to the first portion 1c of the active part 1b of the instrument is an off-centre zone 11 (see FIG. 8).

Figure 10:
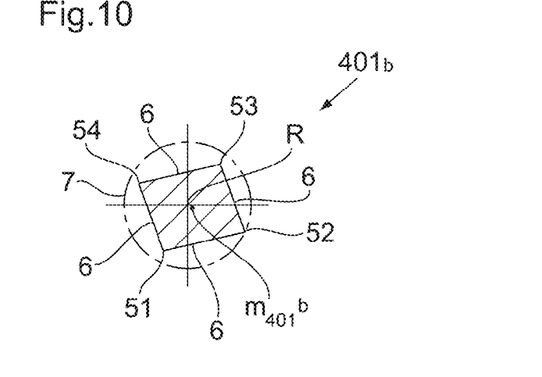
FIG. 10 is a cross-sectional view at the line B-B of the instrument shown in FIG. 8.
Figure 11:
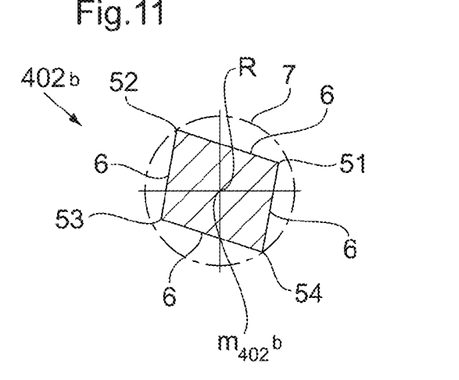
FIG. 11 is a cross-sectional view at the line C-C of the instrument shown in FIG. 8.
Figure 12:
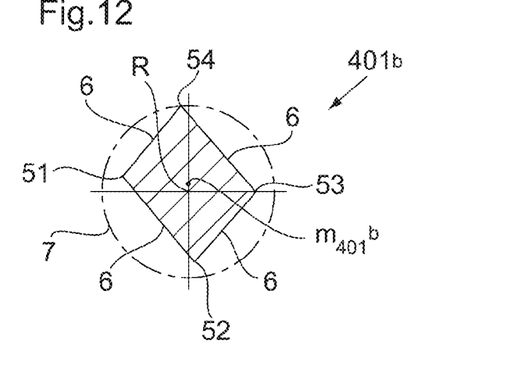
FIG. 12 is a cross-sectional view at the line D-D of the instrument shown in FIG. 8.
Figure 13:
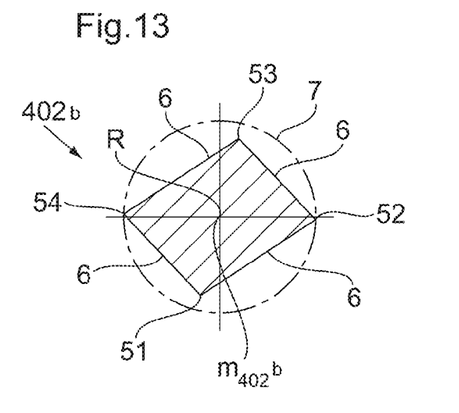
FIG. 13 is a cross-sectional view at the line E-E of the instrument shown in FIG. 8.
Figure 14:
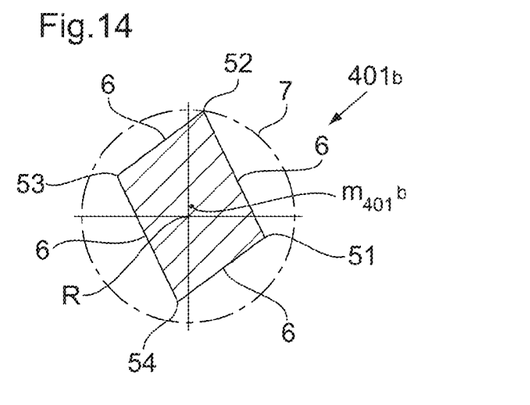
FIG. 14 is a cross-sectional view at the line F-F of the instrument shown in FIG. 8.

FIGS. 11 and 13 each show a cross-section 402b of a centred zone 12 located along the second portion 1d of the active part 1b of the instrument, while FIGS. 10, 12 and 14 each show a cross-section 401b of an off-centre zone 11 located along said second portion 1d.

Preferably, and as shown in FIGS. 11 and 13, for each cross-section 402b of a centred zone 12, two diagonally opposed cutting edges 52, 54 are located on the envelope 7 of the instrument, while the other pair of diagonally opposed cutting edges 51, 53 is located set back within the envelope 7.

In a similar, preferred manner, and as shown in FIGS. 10, 12 and 14, for each cross-section 401b of an off-centre zone 11, a single cutting edge 52, 54 appertaining to the pair of diagonally opposed cutting edges 52, 54 located on the envelope along the first portion 1c of the active part 1b of the instrument is located on the envelope 7 of the instrument, while the other cutting edges are located set back within the envelope 7.

Figure 8:
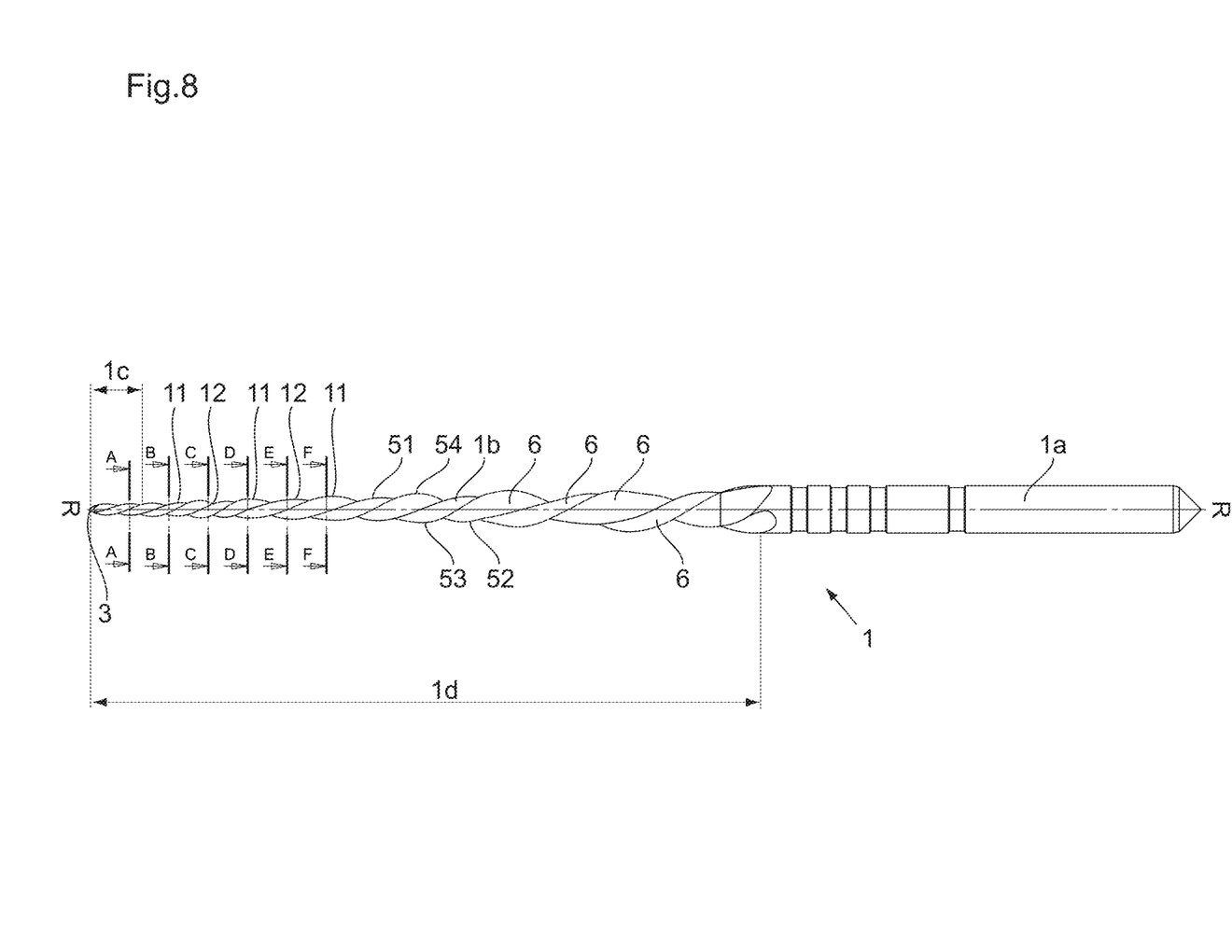
FIG. 8 illustrates a third embodiment of an instrument for drilling dental root canals in accordance with the invention.

Thus, apart from the alternation between the centred and off-centre zones 12,11 on the second portion 1d of the active part 1b of the instrument, in this third embodiment, said second portion 1d also has an alternating arrangement between the cutting edges located on the envelope. The succession of the different zones on the second section 1d of the instrument in accordance with the third embodiment can be described as follows:

The first zone of the second portion 1d immediately adjacent to the first portion 1c of the active part 1b of the instrument is an off-centre zone 11. For each cross-section 401b of this off-centre zone 11, only one of the two diagonally opposed cutting edges 52, 54 located on the envelope 7 for any cross-section 40a of the first portion 1c—the first cutting edge 52—is located on the envelope 7 of the instrument, the second of these cutting edges 54 and the second pair of diagonally opposed cutting edges 51, 53 being set back within the envelope 7 (FIG. 10);

The second zone is a centred zone 12. For each cross-section 402b of this centred zone 12, the first and second diagonally opposed cutting edges 52, 54 are again on the envelope 7 of the instrument, the second pair of diagonally opposed edges 51, 53 still being set back within the envelope 7 (FIG. 11);

The third zone is again an off-centre zone 11. However, in this zone the second cutting edge 54 diagonally opposed to the first 52 and which was set back within the envelope on the first zone is now located on the envelope 7, while the first cutting edge 52 is then located within the envelope 7, the second pair of diagonally opposed cutting edges 51, 53 still being set back within the envelope 7 (FIG. 12).

The following zone shown in FIG. 13 is similar to the first zone and the alternating arrangement thus extends along the second portion 1d of the active part 1b of the instrument.

Thus the instrument in accordance with the third embodiment has two cutting edges 52, 54 which are located on the envelope for any cross-section 40a of the first portion 1c of the active part 1b and for any cross-section 402b of the centred zones 12 of the second portion 1d of the active part 1b but of which at least one of the two is set back within the envelope 7 for any cross-section 401b of an off-centre zone 11 of the second portion 1d, two off-centre zones 11 separated by a centred zone 12 not having the same cutting edge on the envelope 7.

In variations, the second pair of diagonally opposed cutting edges 51, 53 could be located on the envelope 7 of the instrument for any cross-section of the active part 1b or for any cross-section of the first portion 1c or for any centred cross-section 12 of the second portion 1d. The second pair of diagonally opposed cutting edges 51, 53 could also follow the same alternating arrangement described above as the first pair of cutting edges 52, 54 along the second portion 1d of the active part 1b of the instrument.

The other considerations relating to the first two embodiments remain valid for this third embodiment.

In particular, the first portion 1c of the active part preferably extends over a length of 3 millimeters from the point 3 of the active part 1b. In a still more preferred manner, said first portion 1c has a length of 1 millimeter.

Thus as in the first two embodiments described above, the instrument in accordance with the third embodiment is effective since it has a point 3 which is centred and does not generate beating in the canal and permits precise shaping of said canal. Said instrument is also flexible at the rear owing to the presence of the off-centre zones on the second portion 1d of its active part 1b. However, in contrast to the first two embodiments in which the whole of the second portion 1d is off-centre and thus may generate a beating motion at the rear of the instrument, the alternating arrangement of centred and off-centre zones as described in the third embodiment makes it possible to ensure that the instrument is flexible while avoiding beating by ensuring the shape of the envelope generated by the instrument in rotation. Thus the instrument in accordance with the third embodiment retains all the advantages described in relation to the first two embodiments while reducing the beating motion at the rear of the instrument, a motion which could reduce the precision and speed of treatment of the dental root canal.

The embodiments presented above describe polygonal cross-sections with straight sides. It is clear that said sides could be curved. Consequently, the term "polygonal" should be understood in its general sense meaning "which has a plurality of sides" and covering equally a geometric shape with straight or curved sides.

The instrument in accordance with the invention could obviously have other known features such as variable conicity. Similarly, the flutes can be oriented equally to the right or left or even have a variable pitch.

In a general manner, the active part of an instrument in accordance with the invention has, over is whole length, a polygonal cross-section forming at least two cutting edges. The active part is defined by an essentially conical or cylindrical envelope, the longitudinal axis of which coincides with the axis of rotation of the instrument. The active part comprises a first portion extending from the point of the instrument and which is such that any cross-section of this first portion has its centre of mass on the axis of the envelope and defines at least two cutting edges which are all located on said envelope. The active part also comprises a second portion extending following the first portion towards the rear of the active part and which is such that at least one cross-section of this second portion has a centre of mass which is not located on the axis of the envelope but which is offset with respect to this axis and defines cutting edges, of which at least one is located on the envelope and at least one is located set back within said envelope.

The instrument in accordance with the invention thus has a point which is centred with respect to the axis of rotation of the instrument and a rear part, of which at least one cross-section is off-centre. The centred point makes it possible to follow the initial path of the root canal, to avoid any beating motion within said canal in the vicinity of the point and to ensure dimensioning in the preparation of the apical part of the canal. Moreover, the centred point avoids debris descending towards said apical part of the canal and contributes to successful evacuation thereof. This evacuation is further facilitated by the fact that at least one cross-section of the rear part is off-centre: the debris in fact has more space to be carried out of the canal and the off-centring of at least one cross-section of the rear part of the instrument creates a dynamic effect which lifts the debris out of the canal.

Moreover, an instrument in accordance with the present invention makes it possible to ensure strength in the part close to the point in order thus to reduce the risk of breaking the instrument in its most fragile portion. The flexibility of the instrument is not thereby reduced, since the second portion having at least one off-centre cross-section of the instrument makes the instrument flexible and this flexibility can even be progressive towards the rear of the instrument either by adjusting the off-centring of the second portion of the active part of the instrument as described in the case of the first and second embodiments or by alternating centred cross-section with off-centre cross-section along the second portion of the active part of the instrument as described in the third embodiment. Thus the instrument can be rendered sufficiently flexible to follow the complex contour of a dental root canal.

Finally, the active cutting edges of the point of the instrument, i.e. those which are located on the envelope, ensure a good level of efficacy of the instrument. At the rear, the contact zones of the instrument are reduced since some of the edges are located set back within the envelope of the instrument, which makes it possible to reduce the screwing effect and superfluous forces on the rear part of the instrument.

Thus a high-performance instrument is produced having a good balance between efficacy, flexibility and resistance to breaking and to the screwing effect.

The invention claimed is:

1. An instrument for drilling dental root canals comprising:
   a tapered rod defined by a single continuous taper function and having over at least an active part of its length a polygonal cross-section forming at least two cutting edges, said active part terminating by a point and being defined by an envelope of a cylindrical or conical shape along its entire length, the longitudinal axis of the envelope coinciding with the axis of rotation of the instrument,
   wherein for any cross-section of the active part, at least one of the at least two cutting edges is located on the envelope,
   said active part has a first portion extending from the point and a second portion extending following the first portion towards the rear of the active part,
   any cross-section of the first portion has a center of mass located on the axis of rotation, said at least two cutting edges defined by said cross-section of the first portion being located on the envelope,
   at least one cross-section of the second portion has a center of mass offset with respect to the axis of rotation, at least one cutting edge defined by said cross-section of the second portion being located set back within the envelope.

2. The instrument as claimed in claim 1, wherein any of the cross-sections of the second portion has a center of mass offset with respect to the axis of rotation, and
   at least one cutting edge defined by said cross-section of the second portion is located set back within the envelope.

3. The instrument as claimed in claim 2, wherein exactly one cutting edge defined by any of the cross-sections of the second portion of the active part is located on the envelope.

4. The instrument as claimed in claim 3, wherein one of the cross-sections of the second portion of the active part that is located close to the point has a center of mass proportionally closer to the axis of rotation than the center of mass of one of the cross-sections of said second portion that is located at the rear of the active part.

5. The instrument as claimed in claim 2, wherein one of the cross-sections of the second portion of the active part that is located close to the point has a center of mass proportionally closer to the axis of rotation than the center of mass of one of the cross-sections of said second portion that is located at the rear of the active part.

6. The instrument as claimed in claim 1, wherein the second portion has an alternating arrangement of
   centered zones in which any cross-section has a center of mass on the axis of rotation and said at least two cutting edges defined by said cross-section of the centered zones are located on the envelope, and
   off-center zones in which any cross-section has a center of mass offset with respect to said axis of rotation and at least one cutting edge defined by said cross-section of the off-center zones is located set back within the envelope.

7. The instrument as claimed in claim 6, wherein the off-center zones alternate between
   first zones in which for any cross-section a first of the at least two cutting edges defined by said cross-section of the first zones is located set back within the envelope while the second of the at least two cutting edges is located on the envelope, and
   second zones in which for any cross-section, the second of the at least two cutting edges defined by said cross-section of the second zones is located set back within the envelope while the first cutting edge is located on the envelope.

8. The instrument as claimed in claim 1, wherein the active part has over its entire length a polygonal cross-section with straight sides.

9. The instrument as claimed in claim 1, wherein the first portion of the active part has a square cross-section, and
the second portion of the active part has a rectangular cross-section.

10. The instrument as claimed in claim 1, wherein the first portion of the active part has a length between 1 and 3 millimeters.

* * * * *